United States Patent [19]

Faulkner

[11] 4,370,484
[45] Jan. 25, 1983

[54] SCEPTRIN AN ANTIMICROBIAL AGENT FROM *AGELAS SCEPTRUM*

[75] Inventor: D. John Faulkner, La Jolla, Calif.

[73] Assignee: The Regents of the University of California, Berkeley, Calif.

[21] Appl. No.: 242,728

[22] Filed: Mar. 12, 1981

[51] Int. Cl.³ .......................................... C07D 403/14
[52] U.S. Cl. .................................... 548/316; 548/336
[58] Field of Search ................................ 548/316, 336

[56] References Cited

PUBLICATIONS

Burkholder, P., in *Biology and Geology of Coral Reefs, Biology* I, Jones, O., et al. (editors), Academic Press, NY, 1973, 144–155.
Minale, L., et al., *Prog. Chem. Nat. Prod.*, 1976, 33, 1.
Forenza, S., et al., *Chem. Comm.*, 1971, 1129.
Cullen, E., et al., *Can. J. Chem.*, 1975, 53(11), 1690–1691.
Garcia, E., et al., *Chem. Comm.*, 1973(3), 78–79.

*Primary Examiner*—Richard A. Schwartz
*Attorney, Agent, or Firm*—Joseph E. Mueth

[57] ABSTRACT

A novel antimicrobial agent having the formula:

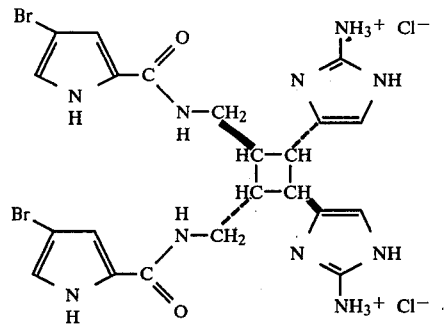

The new antimicrobial agent may exist as the dihydrochloride salt, as shown or as tautomers of the structure, or in the form of other salts and derivatives such as amides and is normally associated with water of crystallization.

The novel antimicrobial agent is obtained from *Agelas sceptrum, Agelas conifera, Agelas schmidti,* an unknown sponge species from Canton atoll and an unknown sponge *Axinella* sp., from Belize.

5 Claims, No Drawings

SCEPTRIN AN ANTIMICROBIAL AGENT FROM AGELAS SCEPTRUM

The invention described herein was made in the course of, or under, a grant from the National Institutes of Health.

BACKGROUND OF THE INVENTION

During a study of Caribbean sponges, several sponges of the genus Agelas were examined and all gave ethanolic extracts having antimicrobial activity, in agreement with previous reports. Burkholder, P. R. in "Biology and Geology of Coral Reefs, Biology I"; Jones, O. A.; Endean, R., Eds.; Academic Press: New York, 1973; p. 144. Prior studies by Minale et al., Minale, L.; Cimino, G.; de Stefano, S.; Sodano, G. Prog. Chem. Nat. Prod. 1976, 33, 1 resulted in the identification of 4,5-dibromo-2-cyanopyrrole as the antimicrobial constituent of the Mediterranean sponge Angelas oroides. A. oroides also contained 4,5-dibromopyrrole-2-carboxylic acid, Forenza, S. L.; Minale, L.; Riccio, R.; Fattorusso, E. Chem. Commum. 1971, 1129, the corresponding amide, and oroidin having the formula:

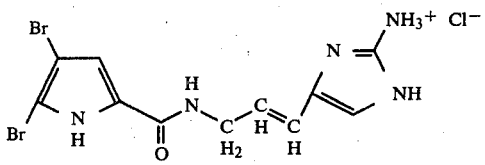

According to this invention, we have now discovered the major antimicrobial constituent of Agelas sceptrum (Lamarck), Agelas conifera, Agelas schmidti, an unknown sponge species from Canton atoll in the South Pacific (collection No. 78-012) and an unknown sponge, Axinella sp., from Belize which have been found to possess superior antimicrobial properties.

SUMMARY OF THE INVENTION

Briefly, the present invention comprises a novel antimicrobial agent having the formula:

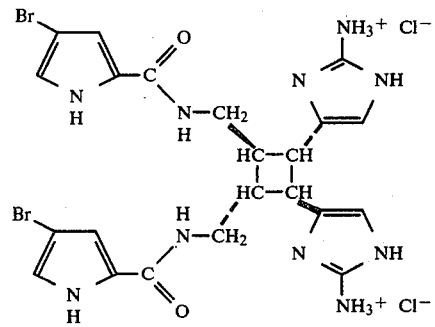

the free amine of the above compound, other tautomers, other salts and amides of said free amine, and each of said compounds associated with water of crystallization.

It is an object of this invention to provide a novel antimicrobial agent.

It is also a further object of this invention to provide a novel preparation of the antimicrobial agent.

These and other objects and advantages of this invention will be apparent from the detailed description which follows.

DESCRIPTION OF THE PREFERRED EMBODIMENTS

The source of the compound of the above formula is from Agelas sceptrum (Lamarck), Agelas conifera, Agelas schmidti, an unknown sponge species from Canton atoll in the South Pacific, and an unknown sponge, Axinella sp., from Belize.

The dihydrochloride can be converted to the free amine by reaction with a stoichiometric amount of a base such as sodium hydroxide which eliminates two moles of HCl. The diamide can be formed by reaction of the free amine with a stoichiometric amount of a lower aliphatic monocarboxylic acid anhydride. For example, the diacetate of the free amine is obtained by reaction of the free amine with two moles of acetic anhydride. Other such acids containing from 1 to about 10 carbon atoms can be used. Salts other than the dihydrochloride can be made by neutralization of the free amine with mineral acids such as dilute sulfuric acid.

The compound, as isolated, is normally associated with several moles of water as water of crystallization. The invention comprehends all such compounds with or without water of crystallization.

The following example is intended solely to illustrate the invention and should not be regarded as limiting in any way. In the Example, the parts and percentages are by weight unless otherwise indicated.

EXAMPLE

Agelas sceptrum, collected at Glover Reef, Belize, was maintained frozen until required. The lyophilized sponge was extracted sequentially with hexane, dichloromethane, and methanol. The acetone-insoluble portion of the methanolic extract was twice chromatographed on Sephadex LH-20 using first methanol then 1:1 methanol/chloroform as eluants to obtain a fraction containing the antimicrobial material. This fraction was chromatographed on a LiChrosorb DIOL column using 1:1 methanol/chloroform as eluant to obtain oroidin (0.01% dry weight) and a compound of the formula:

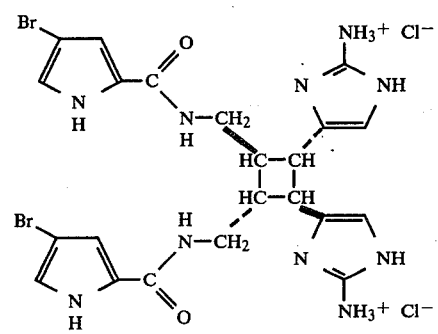

(0.1% dry weight). The compound of the foregoing formula is hereinafter referred to as a sceptrin. Traces of a colored impurity were removed by passing an aqueous solution of sceptrin through Sephadex G-10, after which it was crystallized from water. Sceptrin, mp. 215°–225° C. (dec.), $[\alpha]_D$ −7.4° (c 2.5, MeOH), had the molecular formula $C_{22}H_{24}Br_2N_{10}O_2 \cdot 2HCl \cdot nH_2O$. The elemental analysis of a sample dried at 110° C. over P$_2$O$_5$ required one molecule of water per sceptrin molecule while the x-ray study indicated three water molecules per sceptrin. The electron impact mass spectrum did not show a molecular ion but the field desorption mass spectrum contained a triplet at m/z 619, 621, 623 (C$_{22}$H$_{25}$Br$_2$N$_{10}$O$_2$)$^+$. The following spectral data indicated that sceptrin was a symmetrical dimer of oroidin: IR (KBr) 3350, 1680, 1625 cm$^{-1}$; UV (MeOH) 265 nm ($\epsilon$ 20,850); $^1$H NMR (DMSO-d$_6$) $\delta$ 2.29 (b s, 1 H), 3.10 (d, 1 H, J=8 Hz), 3.42 (b s, 2 H), 6.66 (s, 1 H), 6.97 (s, 1 H), 6.99 (s, 1 H), 7.33 (b s, 2 H), 8.59 (b t, 1 H, J$\approx$5 Hz); $^{13}$C NMR (D$_2$O) $\delta$ 160.8 (s), 145.7 (s), 123.9 (s), 121.6 (d), 111.6 (d), 108.3 (d), 95.2 (s), 41.6, 40.9, 36.9.

Sceptrin crystallized in the monoclinic crystal class and accurate cell constants determined by a least-squares fit of 15 high angle reflections were a=19.788(8), b=13.337(4), and c=13.725(7) Å and $\beta$=122.69(2)°. Systematic extinctions (h+k=2n), a calculated density of 1.63 g/cm$^3$, and the presence of chirality were uniquely accomodated by the space group C2 with four molecules of C$_{22}$H$_{26}$Br$_2$Cl$_2$N$_{10}$O$_2$.3H$_2$O per unit cell. All unique diffraction maxima with 2$\theta$$\leq$100° were collected on a computer-controlled four-circle diffractometer using graphite monochromated CuK$\alpha$ (1.54178 Å) radiation and a variable speed $\omega$-scan technique. Of the 2172 unique reflections surveyed in this fashion, 1697 (78%) were judged observed [F$_o$$\geq$3 (F$_o$)] after correction for Lorentz, polarization, and background effects.

A phasing model was achieved by standard heavy-atom procedures. The following library of crystallographic programs was used: Germain, G., Main, P.; Woolfson, M. M. *Acta Cryst.* 1970, B24, 274 (MULTAN); Hubbard, C. R.; Quicksall, C. O.; Jacobson, R. A. "The Fast Fourier Algorithm and the programs ALFF, ALFFDP, ALFFT and FRIEDEL", USAEC Report IS-2625; Institute for Atomic Research, Iowa State University, Ames, Ia, 1971; Busing, W. R.; Martin, K. O.; Levy, H. A. "A Fortran Crystallographic Least Squares Program", USAEC Report ORNL-TM-305; Oak Ridge National Laboratory, Oak Ridge, Tn., 1965; Johnson, C. "ORTEP: A Fortran Thermal-Ellipsoid Plot Program", USAEC Report ORNL-3794; Oak Ridge, Tn. 1965. The deconvolution of the Patterson synthesis gave the Br positions. The remaining non-hydrogen atoms were located in subsequent electron density maps. Full-matrix least-squares refinement with anisotropic temperature factors for the non-hydrogen atoms, isotropic hydrogens, and anomolous dispersion corrections have converged to a standard crystallographic residual of 0.090 for the structure and 0.094 for the enantiomer.

The two-fold axis of the sceptrin molecule is coincident with the crystallographic two-fold axis. Thus, only half of the atoms in one molecule are independent and the asymmetric unit of the cell contains two such independent C$_{11}$H$_{13}$BrClN$_5$O groups. A drawing of the final x-ray model for one molecule of sceptrin is given. Bond distances and angles agree well with generally accepted values.

Antimicrobial assays of the crude extracts of six Agelas samples revealed the presence of active compounds in all samples. However, when the crude extracts were partitioned between ethyl acetate and water, *A. sceptrum* was particularly distinguished by the strong antimicrobial activity of the aqueous phase.

Sceptrin exhibited antimicrobial activity against *Staphylococcus aureus* (MIC 15 $\mu$g/ml), *Bacillus subtilis, Candida albicans, Pseudomonas aeruginosa, Alternaria* sp. (fungus), and *Cladosporium cucumerinum*. The antimicrobial activity of sceptrin was considerably greater than that recorded for oroidin.

Acute toxicity studies in mice indicated that sceptrin was not toxic at a level of 50 milligrams per kilogram.

The novel antimicrobial agent can be administered to humans in tablet or capsule form. The drug can also be blended with conventional excipients and the like prior to tableting. The drug can also be formulated into parenteral solutions for injection using the usual liquid pharmaceutical carriers.

Having fully described the invention, it is intended that it be limited only by the lawful scope of the appended claims.

I claim:

1. An antimicrobial agent having the formula:

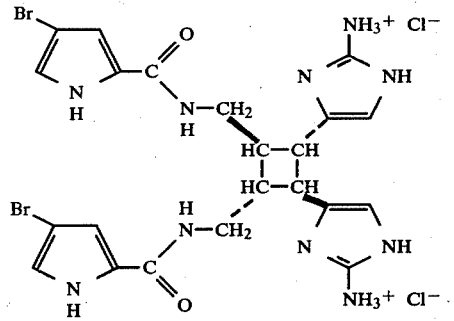

or the free amine thereof, or a lower aliphatic carboxylic acid amide of said free amine, or another mineral acid salt of said free amine, a tautomer of any of said compounds, or any of said compounds associated with water of crystallization.

2. The free amine of the compound of claim 1.

3. The lower aliphatic carboxylic acid diamide of the free amine of the compound of claim 1.

4. The compound of claim 1 in association with water of crystallization.

5. The compound having the formula:

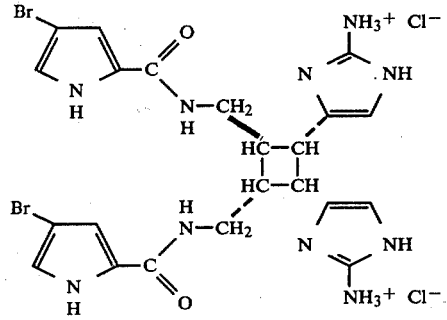

* * * * *